(12) United States Patent
Biellak et al.

(10) Patent No.: US 7,489,393 B2
(45) Date of Patent: Feb. 10, 2009

(54) ENHANCED SIMULTANEOUS MULTI-SPOT INSPECTION AND IMAGING

(75) Inventors: Stephen Biellak, Sunnyvale, CA (US); David Shortt, Milpitas, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 65 days.

(21) Appl. No.: 11/071,072

(22) Filed: Mar. 2, 2005

(65) Prior Publication Data

US 2006/0197946 A1 Sep. 7, 2006

(51) Int. Cl.
*G01N 21/00* (2006.01)

(52) U.S. Cl. .................. 356/237.2; 356/237.4

(58) Field of Classification Search ............. 356/237.4, 356/237.5, 237.1, 237.2, 237.3, 237.6, 625; 250/559.45, 548; 359/629
See application file for complete search history.

(56) References Cited

U.S. PATENT DOCUMENTS

| | | | | |
|---|---|---|---|---|
| 4,464,050 A * | 8/1984 | Kato et al. | ............... | 356/239.1 |
| 5,274,434 A * | 12/1993 | Morioka et al. | ......... | 356/237.4 |
| 5,528,360 A * | 6/1996 | Kohno | .................... | 356/237.5 |
| 5,602,400 A * | 2/1997 | Kawashima | ............... | 250/548 |
| 5,621,499 A * | 4/1997 | Shiozawa | .................... | 355/67 |
| 6,084,716 A * | 7/2000 | Sanada et al. | ............... | 359/629 |
| 6,208,411 B1 * | 3/2001 | Vaez-Iravani | ............ | 356/237.2 |
| 6,369,886 B2 * | 4/2002 | Ishikawa et al. | ......... | 356/237.4 |
| 6,538,730 B2 * | 3/2003 | Vaez-Iravani et al. | .... | 356/237.2 |
| 6,774,991 B1 * | 8/2004 | Danko | .................... | 356/237.4 |
| 6,858,859 B2 * | 2/2005 | Kusunose | ............. | 250/559.45 |
| 6,861,660 B2 * | 3/2005 | Almogy et al. | ......... | 250/559.45 |
| 6,956,644 B2 * | 10/2005 | Biellak et al. | ............ | 356/237.4 |
| 2003/0210392 A1 * | 11/2003 | Vaez-Iravani et al. | .... | 356/237.2 |
| 2003/0223058 A1 * | 12/2003 | Leong et al. | ............. | 356/237.2 |
| 2004/0042001 A1 * | 3/2004 | Vaez-Iravani et al. | .... | 356/237.2 |
| 2004/0246476 A1 * | 12/2004 | Bevis et al. | ............... | 356/237.5 |

FOREIGN PATENT DOCUMENTS

EP 806707 A1 * 11/1997

OTHER PUBLICATIONS

Hecht, Eugene, "Optics", 1998, Addison Wesley Longman, Inc. pp. 606-606.*

* cited by examiner

*Primary Examiner*—Tarifur Chowdhury
*Assistant Examiner*—Tara S Pajoohi
(74) *Attorney, Agent, or Firm*—Smyrski Law Group, A P.C.

(57) ABSTRACT

A system and method for inspection is disclosed. The design includes focusing illumination beams of radiation at an optical axis to an array of illuminated elongated spots on the surface at oblique angle(s) of incidence to the surface, performing a linear scan along a linear axis, wherein the linear axis is offset from the optical axis by a not insubstantial angular quantity, and imaging scattered radiation from the spots onto an array of receivers so that each receiver in the array receives scattered radiation from a corresponding spot in the array of spots.

36 Claims, 5 Drawing Sheets

ENHANCED SIMULTANEOUS MULTI-SPOT INSPECTION AND IMAGING

BACKGROUND OF THE INVENTION

1. Field of the Invention

The present invention relates generally to the field of surface inspection, and more particularly to simultaneously illuminating the surface inspected at multiple spots for enhanced anomaly detection.

2. Description of the Related Art

Conventional optical inspection methods employing scanning techniques typically illuminate a single spot on the surface inspected, where the inspection device scans the entire surface of the specimen for anomaly detection. In order to improve the signal-to-noise ratio associated with background scattering, previous designs have reduced the size of the illuminated spot. The result is an increase in the amount of time required to scan over the entire surface using the smaller spot. An increase in scan time is generally undesirable.

One way of addressing the SNR-spot size dichotomy is to employ a massively parallel inspection and imaging system that illuminates the specimen surface at a plurality of spots where scattered light from the spots are imaged onto corresponding detectors in a detector array. Such a massively parallel inspection system can enhance total inspection throughput, and may be further improved for enhanced performance in certain applications. Such a design is presented, for example, in U.S. Pat. No. 6,208,411. It may therefore be desirable to provide an improved multi-spot inspection and imaging system with enhanced characteristics.

With respect to multi-spot inspection and enhanced imaging, one design that improves the functionality of such a system is to employ a first objective for focusing an array of radiation beams to a surface and a second reflective or refractive objective having a large numerical aperture for collecting scattered radiation from the array of illuminated spots. The scattered radiation from each illuminated spot may be focused to a corresponding optical fiber channel so that information about a scattering may be conveyed to a corresponding detector in a remote detector array for processing. For patterned surface inspection, a cross-shaped filter may be rotated together with the surface to reduce the effects of diffraction resulting from a Manhattan geometry. Such a system may employ a spatial filter in the shape of an annular aperture to reduce scattering from patterns such as arrays on the surface. Different portions of the same objective may be used to focus the illumination beams onto the surface and simultaneously collect scattered radiation from the illuminated spots.

Another design that improves the functionality of a multi-spot inspection system uses a one-dimensional array of illumination beams directed at an oblique angle to the surface to illuminate a line of illuminated spots at an angle to the plane of incidence. Radiation scattered from the spots can then be collected along directions perpendicular to the line of spots or in a double dark field configuration, thereby providing enhanced performance and throughput. One such design having this improved simultaneous multi-spot inspection and imaging functionality is illustrated in U.S. Patent Publication 2004/0042001, inventors Mehdi Vaez-Iravani et al., filed Apr. 18, 2002 and published Mar. 4, 2004.

Such a multi-spot inspection system may provide obliquely incident illumination using, for example, individual incident spots focused onto the specimen surface as shown in FIG. 9 herein, but rather than spot centers lying on a line perpendicular to the optical axis, the incident optics are arranged such that the line connecting spot centers is at a 45 degree angle to the optical axis.

Implementation of this "45 degree angle design" can be highly challenging. From FIG. 9, spots 204 are in focus on the specimen surface, and thus the focal plane of the incidence objective is at approximately 45 degrees to the optical axis. Implementation of this orientation, including manufacturing and alignment of the components, can be particularly difficult, expensive, and potentially very time consuming.

It would be beneficial to provide a system for use in microscopy that overcomes the foregoing drawbacks present in previously known systems and provide an optical inspection system design having improved functionality over devices exhibiting those negative aspects described herein.

SUMMARY OF THE INVENTION

According to a first aspect of the present design, there is provided an apparatus and method for detecting anomalies of a surface. The apparatus and method comprise focusing illumination beams of radiation at an optical axis to an array of illuminated elongated spots on the surface at oblique angle(s) of incidence to the surface, performing a linear scan along a linear axis, wherein the linear axis is offset from the optical axis by a not insubstantial angular quantity, and imaging scattered radiation from the spots onto an array of receivers so that each receiver in the array receives scattered radiation from a corresponding spot in the array of spots.

These and other aspects of the present invention will become apparent to those skilled in the art from the following detailed description of the invention and the accompanying drawings.

DESCRIPTION OF THE DRAWINGS

The present invention is illustrated by way of example, and not by way of limitation, in the figures of the accompanying drawings in which.

DETAILED DESCRIPTION OF THE INVENTION

The costs associated with dark-field pattern inspection have increased steadily with enhanced performance. As semiconductor fabrication approaches finer design rule and resolution, the complexity of inspection tasks has increased dramatically, which, in turn, increases the complexity and costs of the optical front end of the inspection tool and of detection electronics. Furthermore, the variety of situations calling for optical inspection means that a versatile optical inspection tool should be compact, have a small foot print and be rugged so that it is less sensitive to vibrations, and integratable with semiconductor processing equipment. Preferably, the system can be used for inspecting surfaces with diffracting patterns thereon such as patterned wafers, as well as surfaces without such patterns such as unpatterned semiconductor wafers. The present design enables faster and more sensitive inspection to be performed at a reasonable cost.

Figure 1:
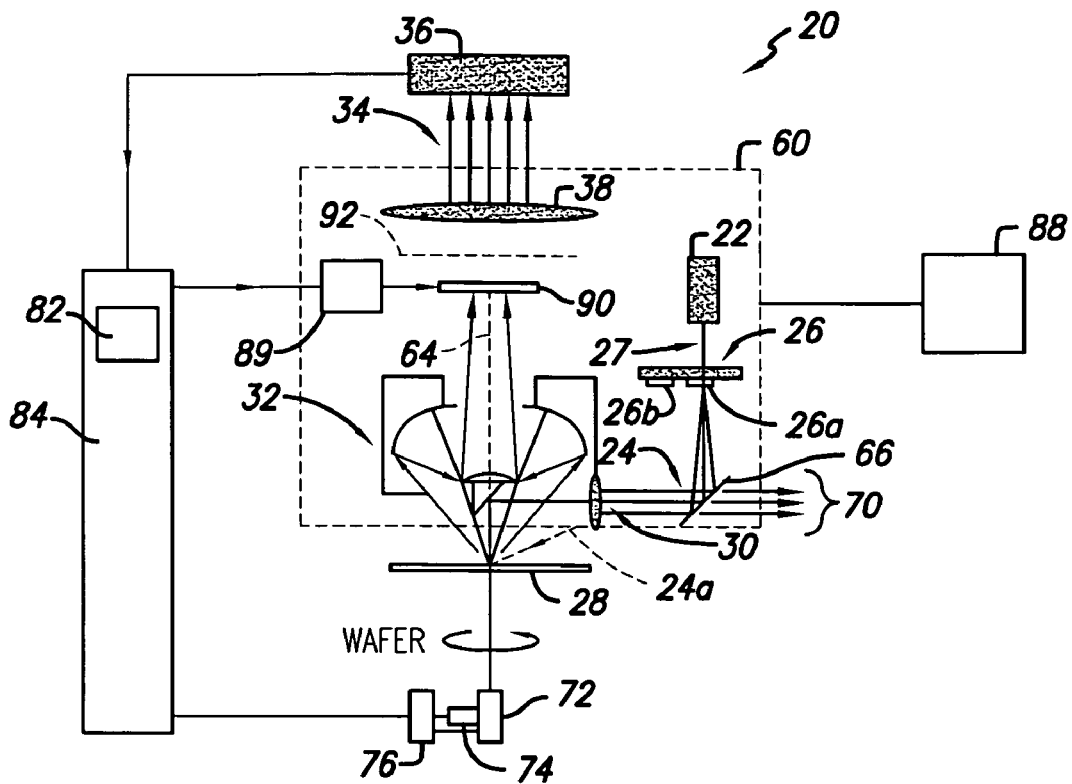
FIG. 1 is a schematic view of a multi-spot dark-field/bright-field inspection and imaging system to illustrate an embodiment of the invention.

The elements of the optical front-end design (such as those in an optical head) of the proposed system 20 are shown in FIG. 1. Radiation from a laser 22 is first split into an array 24 of beams, preferably a two-dimensional array, by the action of a diffractive optical element 26a on substrate 26. These beams are simultaneously focused onto the surface of a specimen or sample or wafer 28, such as a semiconductor wafer, placed on a spinning stage, preferably a precision spinning stage, by a lens such as a simple doublet lens 30. Lens 30 may have a numerical aperture of not more than 0.8. The radiation scattered off each spot may be collected by a reflective lens 32, and imaged by an objective 38 onto a corresponding fiber in an M×N array 34 of optical fibers arranged to correspond to the distribution of the spots on the wafer. These fibers can carry the radiation to an array 36 of avalanche photodiodes (APD), amplifiers, and digitizers. Other types of detectors are possible and may be used as described below.

Figure 2:
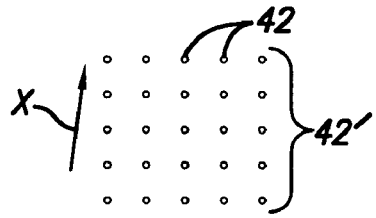
FIG. 2 shows a schematic view of a two-dimensional arrangement of multiple illuminated spots on the surface inspected to illustrate the embodiment of FIG. 1.
Figure 3:
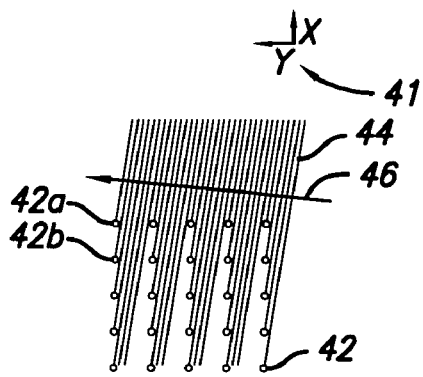
FIG. 3 illustrates a schematic view of the multiple spots of FIG. 2 and their scan paths across the surface inspected to illustrate the embodiment of FIG. 1.
Figure 4:
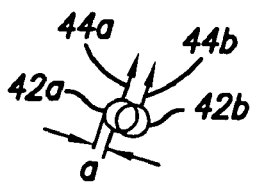
FIG. 4 is a schematic view illustrating the scan paths of two adjacent spots to illustrate the embodiment of FIG. 1.

Alternatively, instead of imaging the scattered radiation collected from each spot on the specimen to an optical fiber, it may be imaged onto a detector in an detector array. In the embodiment of FIG. 1, the illumination beams 24 are directed towards the wafer surface in directions that are substantially normal to the surface of the wafer. The beams may illuminate spots on the specimen surface that are substantially circular in shape The orientation of the spots 42 illuminated by the array 24 of beams is slightly rotated with respect to the tangential direction x of the wafer as the wafer is rotated as shown in FIG. 2, resulting in the"painting" of the spacing along paths 44 between any two adjacent spots along a row with the path taken by the spots along the columns as shown in FIG. 3. In an x-y coordinate system 41, the thick arrow 46illustrates the y direction of the image obtained. The separation between the adjacent spots may be selected so as to satisfy a desired sampling level(e.g. 3×3 or 4×4 samples per point spread function, PSF). This separation is illustrated in FIG. 4, which shows the paths of two adjacent spots, such as spots 42a and 42b in FIG. 2 traveling along paths 44a and 44b, respectively. The two paths may be offset by a separation a substantially equal to one-third or one-quarter of the spot size to achieve the 3×3 or 4×4 samples per point spread function, so that the spots 42a and 42b would overlap by two-thirds or three-quarters of the spot size. Thus, a one-dimensional scan of the wafer produces a two dimensional image, as illustrated in FIG. 3.

The optical components in the design include a multi-beam splitter 26a that may be similar to the grating element employed in the design illustrated in U.S. Pat. No. 6,208,411, namely a specially designed diffractive optical element. In choosing the total number of spots, here 42, total system complexity may be a factor, including costs associated with the electronics. A total of 128 channels can provide adequate performance in such an environment. 128 channels may be achieved using a 16×8 array of spots. Other combinations are also possible. In some applications, the use of an odd number of spots such as 17×9 may be advantageous. The angular orientation of the spots with respect to the tangential direction of the wafer may be such that the spots in the vertical direction traverse the space between any two adjacent horizontally positioned spots (FIG. 2), resulting in a relatively complete coverage of the specimen. Separation between spots may be chosen such that four samples per point spread function (PSF) may be attained in each direction. This is a slightly denser sampling than in the case of the AIT™ system available from KLA-Tencor Corporation of San Jose, Calif. In order to reduce processing time, smaller interpolation kernels may be allowed for the same level of residual interpolator truncation error. A spiral scan can also provide a denser sampling, since the interpolation is inherently more complex than for a rectilinear scanner.

The point spread functions of the spots are Gaussian shaped with a $1/e^2$ intensity width of 5 microns, for example. At a 4×4 sampling level, where the spot separation is about 20 microns, the total widths (i.e. swath) of the tracks of the 128 (for a 16 by 8 array) spots is about 160 microns. In this context, a track is the locus of a spot as the sample is scanned. The maximum amount of the beam fan out in at the focusing lens 30 tends to be so small that only a simple doublet suffices for focusing. Other types of lenses may also be used.

The dark-field collector in this design is a reflecting objective 32 positioned directly above the illuminated field. While a 0.5 numerical aperture (NA) lens may be used for objective 32, lenses of other NA values are possible. The reflecting lens can perform two tasks: collecting the radiation scattered off each point, and imaging the field onto a corresponding array of fibers. Separation of the spots on the specimen is such that they can be considered as completely independent, without inter-spot interferences.

The radiation provided by laser 22 may contain one wavelength component or more than one wavelength component. Such radiation may include a wavelength component in the ultraviolet range, deep ultraviolet range, visible or infrared range, or wavelength components in more than one of these four different wavelength ranges. The laser or other radiation source 22 may operate in the visible, infrared, ultraviolet or deep ultraviolet range or ranges. An attraction of using a reflecting objective such as mirror 32 is that it functions well over a large range of wavelengths. For some applications, a refractive objective may also be used instead of a reflective one for collecting and imaging scattered radiation from the wafer 28 to the fiber array 34.

Laser 22 may emit radiation of substantially a single wavelength. Alternatively, laser 22 may emit radiation of a plurality of wavelengths, although radiation of only one of the plurality of wavelengths is typically employed at any one time for inspection. In such a situation, the wavelength of radiation supplied by the laser for inspection may vary or change. The diffracting element 26a may be placed at the back focal plane of lens 30 so that the beams 24 are focused to the surface of the wafer 28, where the axes of beams 24 are substantially parallel to one another and perpendicular to the wafer surface.

Where radiation of a different wavelength is employed in scanning the specimen surface, such as where laser 22 includes more than one wavelength component, spot separation may change if the same element 26a diffracts the laser beam, since diffraction by element 26a is wavelength dependent. In such event, a different diffraction element such as element 26b may be used to compensate for the change in wavelength so that the spot separation remains substantially the same. Beam forming optics (not shown) may be used to change the width of the beam from the laser in order to maintain the same spot size so that the collection optics in the system need not be changed. This switching between diffracting elements 26a and 26b can be accomplished by moving substrate along direction 27 using means such as a motor (not shown in FIG. 1). Since phase changes are of negligible interest and are typically not detected, element 26b does not need to be aligned precisely with respect to the beam. More than two diffraction elements may be formed on the same substrate 26 in the event the laser beam contains more than two wavelength components.

The same spot separation and spot size previously employed can be achieved by altering the focal length of the focusing lens 30 in FIG. 1 rather than changing the diffracting element when different wavelength radiation is employed. The collection optics may also remain the same. However, since the diffracting element can be placed at the back focal plane of lens 30, alteration of the focal length of the lens can require relocating the element. Relocation places the element at the back focal plane of the lens 30. When changing spot separation and spot size, the wavelength of the radiation used to inspect the wafer may be altered without substantially changing the illumination optics. The imaging optics may then be altered in this arrangement by changing the magnification of the lens 38 so that lens 38 can still focus the collected radiation from the spots and image onto the fibers.

To obtain a different spot separation and spot size without changing the wavelength of the radiation used to inspect the wafer, the focal length of lens 30 may be altered, or the diffracting element and/or beam forming optics can vary. These and other variations are within the scope of the present design.

Laser 22 can emit more than one wavelength component. When more than one wavelength component is emitted, appropriate wavelength selection optical elements such as filters or beam splitters (not shown) may be employed in the path of the beam from laser 22 to obtain the desired wavelength component. Radiation substantially at only one selected wavelength can thus be supplied to element 26a or 26b at any one time. In such an arrangement, laser 22 and wavelength selection optical elements form an optical source supplying selectable wavelength radiation from among a plurality of wavelengths. Other types of optical sources that supply radiation of a selectable wavelength may be used.

Alternatively, where laser 22 emits monochromatic radiation, a different laser emitting radiation of a wavelength different from that emitted by laser 22 may replace laser 22. Also, separate monochromatic or polychromatic lasers may be combined using, for example, dichroic filters to provide radiation of selectable wavelength. Other variations may be employed.

In a system providing enhanced detection sensitivity, the collection optics such as objective 32 may have a relatively large numerical aperture (NA) whereas for the illumination optics such as lens 30, a low NA can be sufficient. System 20 illustrated in FIG. 1 shows a relatively compact design where the illumination optics and collection optics employ different objectives, namely objectives 30 and 32, where the collection objective 32 has a larger NA than illumination objective 30. Using low NA illumination optics can enable both the illumination optics and collection optics to fit within the space close to the specimen or wafer 28 in a particularly compact design of the optical head as shown in FIG. 1.

The optical head in FIG. 1 is relatively compact and has a particularly small "footprint," or overall horizontal (x-y) dimension. Thus, optical head 60 within the dotted line box generally includes a laser 22, diffractive element 26a, lens 30, collection objective 32, and the array of optical fibers 34. In a slightly modified design from that shown in FIG. 1, laser 22 may also be located outside the optical head 60 and may be placed so that the resultant output laser beam is directed to the diffractive element 26a in the optical head 60, possibly by means of an optical fiber link.

The collection objective 32 focuses radiation scattered from each illuminated spot 42 on the surface of specimen or wafer 28 to a corresponding optical fiber in the optical fiber array 34. Information related to the scattered radiation from each spot is then carried by its corresponding fiber to a two-dimensional diode array where the diodes may be avalanche photodiodes. Alternatively, individual fibers may carry signals to individual avalanche photodiodes photomultipliers, photodiodes or other types of individual detectors. By using an optical fiber array 34, the detector array 36 does not need to be included in the optical head 60 and can be located at a distance from the optical head, thereby further reducing the size of the optical head. Alternatively, for applications where spatial considerations are not as important, the optical fiber array 34 may be omitted and the scattered radiation from each spot may be focused directly by objective 32 to a corresponding detector in the detector array 36 within the optical head. Other variations are also possible. Lens 38 focuses the scattered radiation from a spot 42 to the corresponding fiber within the optical array 34.

From the foregoing, element 26a diffracts the laser beam from laser 22 into a two-dimensional array of beams 24. Element 26a may alternately diffract the beam into a one-dimensional array of beams to illuminate a one-dimensional array of illuminated spots on the surface of the wafer 28. Such one-dimensional array of illuminated spots may, for example, comprise the five illuminated spots appearing as the right most column 42' in FIG. 2.

Figure 9:
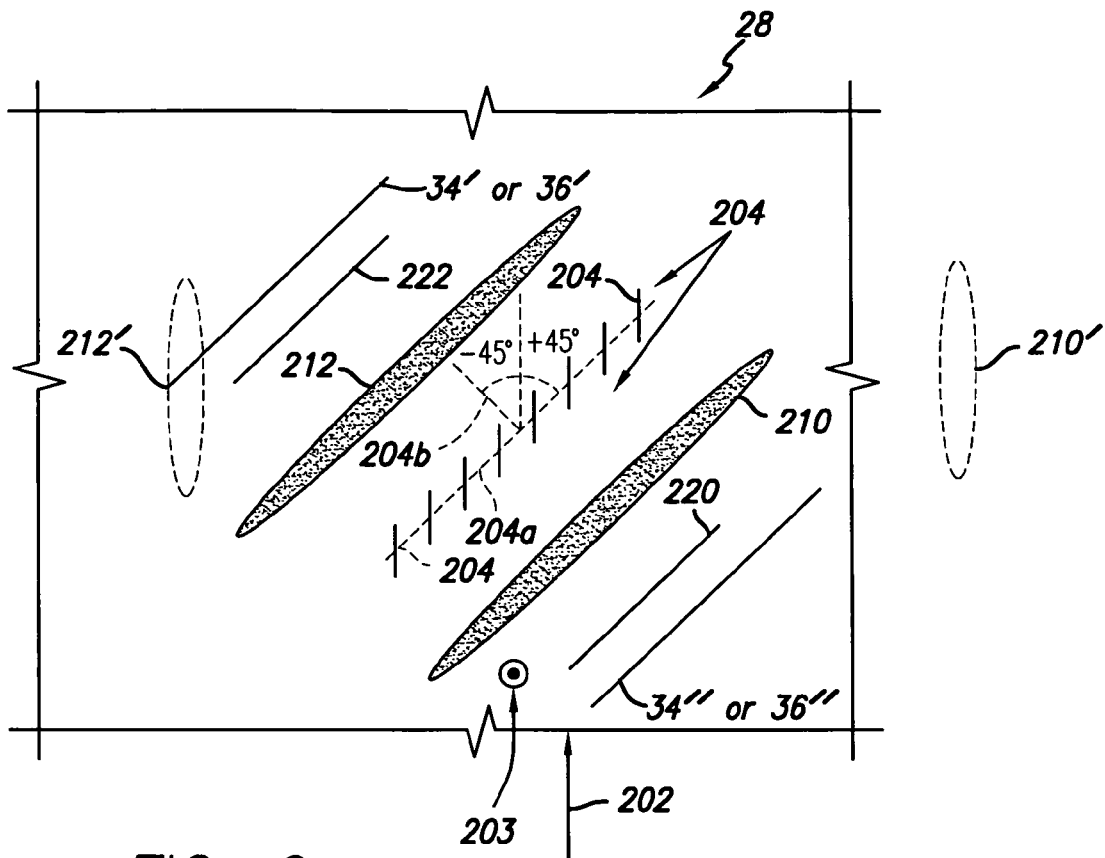
FIG. 9 illustrates a top schematic view of an optical inspection and imaging system to illustrate another embodiment.

Another example of a one-dimensional array of beams and spots is illustrated in FIG. 9. The paths of illuminated spots in column 42' may also overlap as indicated in FIG. 4.

Bright Field/Dark Field Detection

Bright field detection entails detecting specularly reflected radiation, and is described in "Wafer Inspection Technology Challenges for ULSI Technology", S. Stokowski and M. Vaez-Iravani, Proceedings of Conference on Characterization and Metrology for ULSI Technology, American Institute of Physics, pp. 405-415 (1998).

In the embodiment of FIG. 1, the array of illumination beams 24 are focused by lens 30 to a mirror 62 that reflects the beams toward specimen or wafer 28. Mirror 62 also can act as an aperture stop to reduce or prevent specular reflection of the beams from the surface of specimen or wafer 28 from reaching the optical fiber array 34. In such an arrangement, the collection mirror 32 collects only radiation scattered by the spots along collection paths away from the specular reflection direction in a dark field imaging system. Dark field systems collect and detect radiation scattered by the sample or specimen. Radiation is generally collected along collection paths away from the specular reflection direction, wherein light energy is reflected from the sample/specimen surface, where collection paths are "away" relative to the transmitted illumination beams. Dark field systems are explained in more detail in the above-referenced Stokowski and Vaez-Iravani article.

FIG. 1 also shows the reflected path into the bright field channels 70. Bright field channels 70 may comprise an optical fiber array similar to array 34. The beams 24 from element 26a are first reflected by a beam splitter 66 towards lens 30 and mirror 62. Part of the radiation specularly reflected by the specimen or wafer surface is again reflected by mirror 62, collimated by lens 30 and passes through the beam splitter 66 towards bright field channels 70 and to an array of detectors (not shown). As with dark field detection, the radiation reflected from each spot may be imaged by lens 30 onto a corresponding channel in channels 70 and then to a corresponding detector. Also as in the dark field system, the detector array in the bright field system need not be included in optical head 60, and omission of the detector array from the optical head 60 can result in a more compact design. Where space is not as significant a concern, channels 70 may be replaced by an array of detectors so that lens 30 and simple optics (not shown) located downstream from lens 30 (in the same optical path) image radiation reflected by each spot directly to the corresponding detector in the detector array.

Bright field channels may yield useful information on large defects that can be discerned by detecting the reflectance at various spots on the surface of specimen or wafer 28. If bright field inspection at the proposed resolution is employed, appropriate fiber channels can be set up in the same manner as dark field channels using a detector array in addition to array 36. Bright field and dark field radiation could also be detected sequentially using the same electronics. Alternatively, they may be used simultaneously using separate electronics.

Wafer Scanning

Wafer 28 is supported on a chuck (not shown) rotated using, for example, a motor 72 and translated in a direction by gear 74 so that the illuminated spots 42 move and trace a swath of spiral paths on the surface of specimen or wafer 28 to inspect the entire surface of the specimen or wafer 28. Both vacuum handling and edge handling of the samples are possible. Motor 72 and gear 74 are controlled by controller 76 in a manner known to those skilled in the art. The optical head 60 remains stationary. Beams 24 scan across the surface of the specimen or wafer 28 using motor 72, gear 74 and controller 76 to move the wafer and scan the entire wafer surface. Alternatively, the optical head 60 may move in a manner tracing a spiral path or another type of scan path to scan specimen or wafer 28. X-Y stages may be employed to scan the specimen or wafer along substantially linear paths.

As noted, the detector in array 36 may be a photodiode such as an avalanche photodiode, or alternatively, a photomultiplier tube. The output of each detector in the detector array 36 may be supplied to processing circuit 82 where the circuit may comprise a microprocessor, hardware logic or programmable logic circuits, such as those using FPGAs or dynamic logic. Circuit 82 may be a part of or connected to a computer 84 in communication with controller 76 so that scattered radiation from a particular detector in array 36 can be matched with a location on the surface of the specimen or wafer 28. Where processing circuit 82 is a microprocessor, processing circuit 82 can be a co-processor within computer 84. Processing circuit 82 generally stores the outputs and/or signals of detector array 36 and processes the outputs and/or signals, such as by comparing signals in a die-to-die operation for detecting anomalies. Alternately, processing circuit 82 may perform certain initial processing of the signals, such as signal amplification and conversion from analog-to-digital form and passes the digital signals to computer 84 to perform further processing such as die-to-die comparison.

The design in system 20 of FIG. 1 is generally based on a stationary optics as described above, and R/theta spinning of a semiconductor wafer in a manner similar to that in the SP1™ tool, also available from KLA-Tencor Corporation of San Jose, Calif. System 20 may have a rather precise spinning action. For example, the spinner may generally be able to achieve some +/−15 microns stability in height, and uniform spinning on the micron scale. This performance can be achieved by means of an air bearing stage, for example. By scanning the wafer surface with multiple spots simultaneously, the scanning of the entire wafer surface can be performed in shorter time.

This spiral scanning action can begin to deviate from linear motion as the position of the beams approaches the center of a semiconductor wafer. Ramping the rotation rate down toward the center can resolve this issue. Generally, a precise knowledge of the position of any of the beams, such as within one pixel, can enable correcting for the aforementioned scan deviations.

Filters for Reducing Diffraction from Manhattan Geometry and from Pattern(s)

During the beam scanning process, at any given position on the semiconductor wafer, such as specimen or wafer 28, each of the spots 42 can illuminate a number of shapes lying along the Manhattan geometry. These shapes all generate a two dimensional "sinc" function, but with different phases, giving rise to a "+" diffraction pattern. As the wafer rotates, this pattern also rotates. If one were to detect all the available scattered radiation from the wafer, one would also receive parts of this diffraction pattern. In the ensuing die-to-die comparison, the presence of this large background could possibly result in significant errors.

In rectilinear scans, resolution of the aforementioned errors may be achieved using a stationary spatial filter to filter out the speckle pattern. Placing detectors along the 45 degree lines with respect to the horizontal-vertical directions could also minimize errors.

Figure 5:
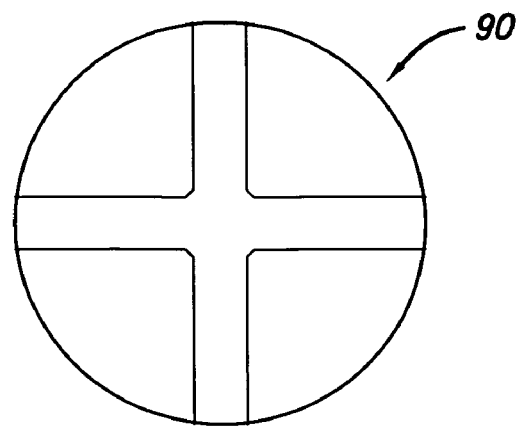
FIG. 5 shows a schematic view of a spatial filter in the collection path of the embodiment of FIG. 1 to further illustrate the embodiment.

In operation, rotation of the wafer 28 results in a rotating diffraction pattern. This pattern can be eliminated or reduced by placing a "+" shaped filter 90 (i.e. a filter having an aperture that passes radiation except for a "+" shaped area), shown more clearly in FIG. 5, directly above the illuminated field in the path of the radiation after emergence from the reflective objective 32. A motor 89 rotates filter 90 under the control of computer 84 in FIG. 1. Rotation by motor 89 operates in unison with the rotation of wafer 28 under the control of controller 76, generally resulting in a continuous cancellation of the diffraction pattern. Possible designs include ball-bearing based systems that can be mounted directly at the exit port of the reflecting objective; a programmable liquid crystal filter having an aperture changing synchronously with the rotational motion of the sample surface under the control of computer 84 to implement filter 90, rather than a mechanically rotated filter as described above. Such a programmable liquid crystal filter design may be viable for low rotation rates of the wafer.

Figure 6:
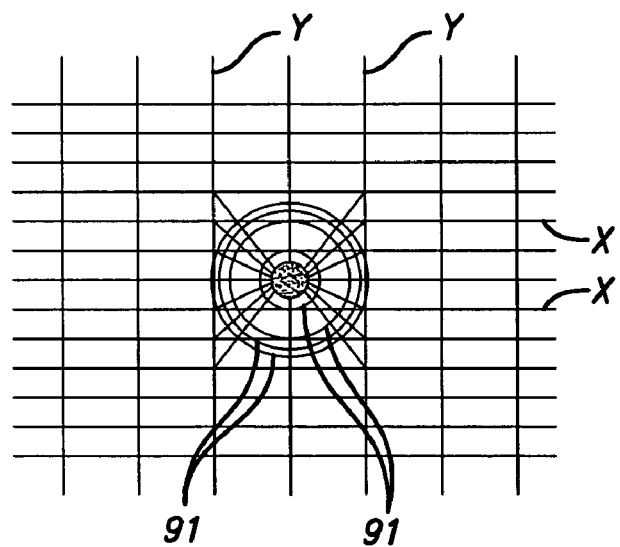
FIG. 6 illustrates a schematic view of an annular-shaped spatial filter that may be used in the in the collection path of the embodiment of FIG. 1.

In addition to diffraction from the Manhattan geometry, the presence of any periodic structures such as DRAM arrays on the surface of the wafer may result in two-dimensional Fourier components when illuminated with normal incidence radiation. If the directions of the expected pattern scattered from the surface are known, spatial filters may be designed to block such scattering, thereby detecting only the scatter by anomalies on the surface. FIG. 6 is a schematic view illustrating the two-dimensional Fourier components of an array structure that is periodic in the X and Y directions when illuminated with normal incidence radiation. As the sample rotates, all of the spots at the intersections of the X-Y lines will rotate, thereby generating circles 91. These circles represent the loci of the Fourier components as the wafer is rotated. The dark opaque circle at the center is the blockage of the collection space caused by stop 62 in FIG. 1.

From FIG. 6, no gaps exist in between the circles where there are no Fourier components. One may construct a programmable filter (e.g. a liquid crystal filter) that blocks out annular bands of arbitrary radii. A simple spatial filter may also achieve many of the filtering functions described herein. Thus, if the cell size of a regular memory array on the wafer is such that its X and Y dimensions are not larger than about 3.5 microns, for example, this means that for 488 nanometers wavelength radiation used in the illumination beams 24, the first Fourier component is at about 8 degrees to the normal direction 64. Therefore, if a spatial filter such as 92 of FIG. 1 is employed, blocking all collected radiation in the narrow channel that is at 8 degrees or more to the normal direction 64 can leave an annular gap of 2 or 3 degrees ranging from the rim of the central obscuration (i.e. 5 or 6 degrees) to the rim of the variable aperture at about 8 degrees. Under these conditions, as the wafer spins, virtually no Fourier components can penetrate the annular gap and scatter from the array can be suppressed. The spatial filter 92 in FIG. 1 can leave an annular gap between about 5 to 9 degrees from the normal direction 64 to the surface of specimen or wafer 28 in FIG. 1. For DRAM structures of smaller cell sizes, such annular aperture type spatial filtering may be omitted. While both filters 90 and 92 are shown in FIG. 1, for certain applications, use of only one of the two filters may be adequate and is within the scope of the present design.

Even though the collection objective 32 focuses radiation scattered from an array of spots 42, such scattered radiation from the spots are generally focused towards the optical fiber array 34 through a small area at the focal plane of the objective. By placing filter 90 and/or filter 92 at or close to the focal plane, the aforementioned functionality and effects can be realized with respect to the scattered radiation from all of the illuminated spots 42 in the array of spots.

Detection Channels and Processing Circuit

Individual avalanche photodiode detectors (APDs) may be used as detectors in array 36 for each of the dark-field channels. These detectors provide close to shot noise limited performance. If bright-field channels are considered important, then a separate APD board may be provided for those, or an array of PIN diodes.

Each APD channel may have a voltage setting and analog-to-digital converter (ADC) operational at up to 60 MHz. The data rate potential of such a design approaches 5-10 GHz, even though a practical data rate may be somewhat lower. The detection electronics part of the design in this case may be completely separate from the front-end optics, such as the optical head 60. This separation can provide a simple, compact, and robust design. The optical head 60 may be readily integrated into semiconductor processing equipment 88, enhancing detection of anomalies on the specimen or wafer surface during processing or between processing steps using semiconductor processing equipment 88.

Detected signals may be directed into a massive bank of random access memory (RAM) in circuit 82, capable of holding up to 85 Gbytes of data. Data may be gathered from the various dice at different locations on a semiconductor wafer as the wafer is scanned. Subsequent image processing is primarily based on a die-to-die comparison process, applied to side-by-side dice, in a rectilinear direction, much in the same way as that in conventional systems, such as the AIT™ systems available from KLA-Tencor Corporation of San Jose, Calif.

Because scanning occurs in a spiral rather than rectilinear fashion, the die-to-die comparison may be performed on a stored version of the 12-bit gray scale data. Data from the entire wafer does not need to be stored. Only a sufficient quantity of data enabling die-to-die comparison on the present location is needed. For some applications, memory sufficient to store an entire wafer map may be employed. At a pixel size of 1.25×1.25 microns, a 300 mm wafer has approximately 45 gigapixels. To store all pixels as 12-bit values, some 70 GB of memory may be needed. Processing power should be sufficient to support the pixel rate. A typical pixel rate for some embodiments can be about 1 Gpixels/sec, and higher speeds are also possible.

Where scanning is non-rectilinear, retaining image data for a single swath in order to perform die-to-die comparison may not be possible. However, by retaining all pixel information for the specimen or wafer upon receipt, and by concurrently comparing incoming pixels with those of a reference die chosen so that pixels are acquired slightly sooner in time, each die can be compared with a reference die during the scan. Once the spiral scan is complete, processing will be nearly finished.

Figure 7:
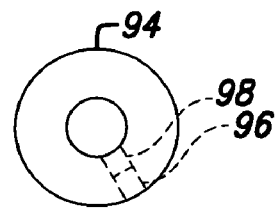
FIG. 7 is a schematic view of an annular-shaped illuminated region of the surface inspected containing two dice to illustrate one aspect of the embodiment of FIG. 1.

A reference die may be chosen so that its pixels are acquired slightly sooner in time. In this manner, each die can be compared with a reference die during the scan. FIG. 7 which is a schematic illustration of data obtained from an annular region 94 of a semiconductor wafer. The specimen or wafer may be scanned beginning at a point on or near the circumference of the specimen or wafer, or at or near the center of the specimen or wafer. Assuming that the spiral path scan of the array of spots 42 starts out at the circumference of the wafer and spirals in toward the center of the wafer during the scanning, a reference die 96 may be defined at or close to the outer circumference of the annular region 94. When the data from the target die 98 is obtained, such data may be compared to the data in the reference die obtained earlier for anomaly detection. Die-to-die comparison(s) using dice data acquired earlier from a reference dice different from dice 96 may be used instead.

Figure 8:
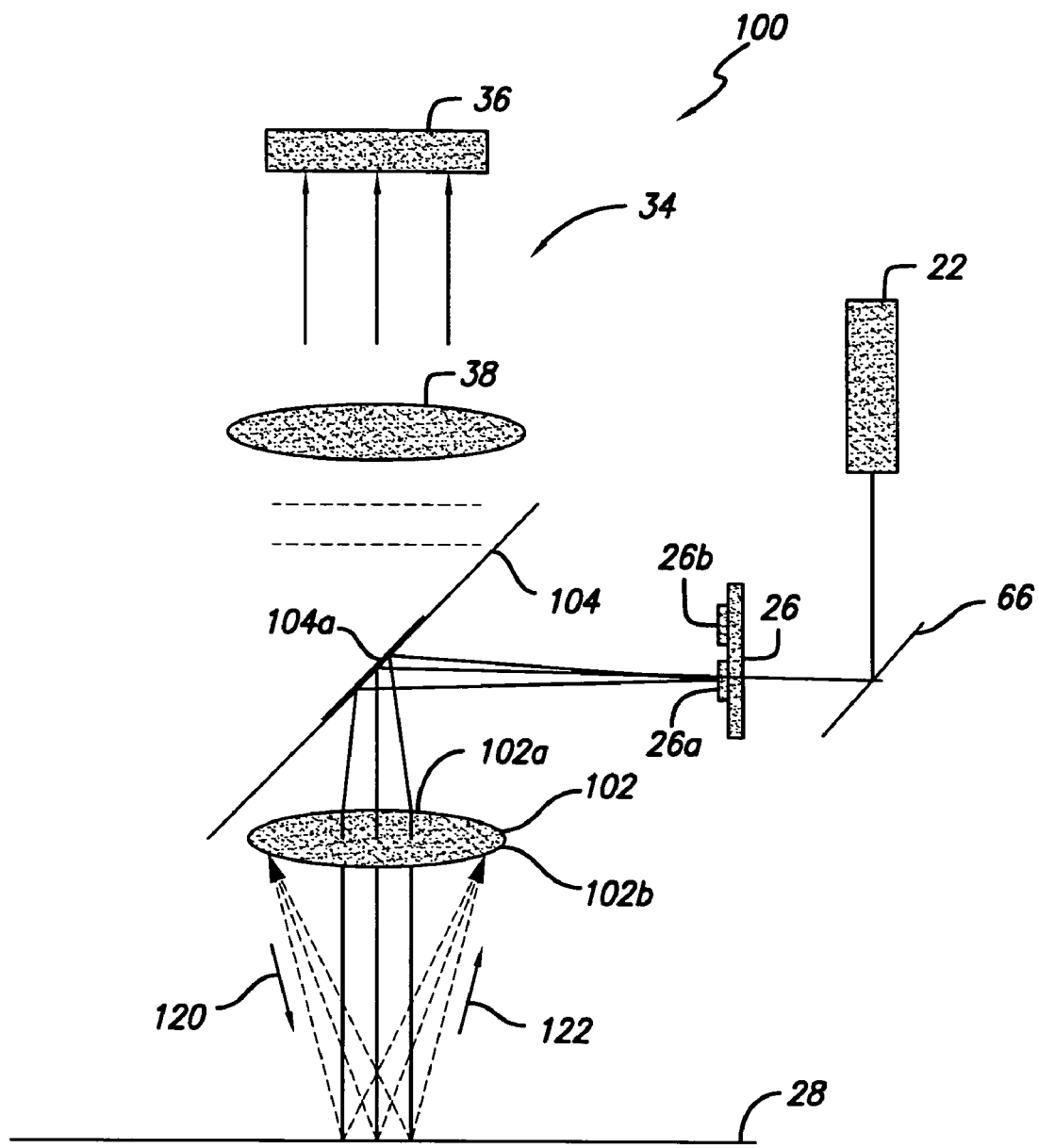
FIG. 8 presents a schematic view of an optical inspection and imaging system.

FIG. 8 is a schematic diagram of an optical inspection and imaging system. Instead of using two separate objectives, one for illumination and the other for collection, the design 100 of FIG. 8 employs a single objective for this purpose, although different portions of the objective 102 may be employed for illumination and for collection. Thus, as shown in FIG. 8, a laser beam from laser 22 may be reflected by a mirror or beamsplitter 66 and diffracted into an array of beams 24 using diffractive element 26a. Beams 24 are reflected by a center reflective portion 104a of beamsplitter 104 to lens 102. Beams 24 may be focused by a center portion 102a of the aperture of lens 102 to the surface of specimen or wafer 28. Scattered radiation from the illuminated spots 42 may be collected by lens 102 and directed towards the beamsplitter 104. The center reflective portion 104a acts as an aperture stop preventing specular reflection from the specimen or wafer surface from reaching the optical fiber array 34. Thus, only the scattered radiation collected by the circumferential portion 102b of the aperture of lens 102 can pass through the beamsplitter 104 and be focused by lens 38 towards the optical fiber array 34. The portion 102b for collecting scattered radiation may be larger than the portion 102a used for illumination, enhancing detection sensitivity.

To simplify FIG. 8, the components shown in FIG. 1 for moving the wafer, the bright field channels, the processing circuit and computer have been omitted from the figure. The design 100 of FIG. 8 is more compact compared to the design of FIG. 1, since a single objective is used for both illumination and collection. Instead of using a lens as shown in FIG. 8, a reflective objective may be employed to ensure relatively easy operation and a large wavelength range. Instead of using a center portion 102a for focusing the illumination beams and a circumferential portion 102b for collecting the scattered radiation, the arrangement in FIG. 8 can direct the illumination beams 24 through a side portion of the objective, such as the left side of the objective 102. The other side, such as the right side, may be used for collection of the scattered radiation. Where the paths of illumination beams are at oblique angles to the surface of specimen or wafer 28, at least one dimension of the illuminated spots may be not less than about 5 microns.

For the design shown in FIG. 1, the illumination beams 24 are directed toward the wafer surface in directions substantially normal to the surface of the specimen or wafer. For some applications, illumination beams may be directed towards a surface at an oblique angle such as along the paths 24a indicated by the dotted line in FIG. 1 so that at least one dimension of the illuminated spots is not less than about 5 microns. Particularly for the inspection of surfaces such as unpatterned wafer surfaces, illuminating the wafer surface at an oblique angle may be desirable.

As shown in FIG. 9, a single line of illumination beams is supplied at an oblique angle along direction 202 to the surface of specimen or wafer 28, only a portion of which is shown in FIG. 9. The single line of illumination beams (not shown) illuminate a single file array of elongated illuminated spots 204 on the surface of the wafer. The beamsplitter (not shown in FIG. 9) used to generate the single file array of elongated illuminated spots 204 is oriented at or near an angle, such as 45 degrees, for example, relative to the plane of incidence of the illumination beams, so that the line 204a connecting the centers of the elongated illuminated spots 204 is also at or near 45 degrees with respect to the plane of incidence. In this orientation, the plane of incidence is defined by a plane containing the illumination direction 202 and a line 203 (pointing out of the plane of the paper) intersecting direction 202 and normal to the surface of the specimen or wafer 28. Thus, if direction 202 is regarded as an axis of a coordinate system, the line 204a connecting the centers of the spots 204 is substantially at +45 degrees to such axis.

Radiation scattered from the spots 204 may be collected along directions substantially perpendicular to line 204a by objectives 210 and 212 located above the plane of the surface inspected and on opposite sides of line 204a. Objective 210 images the scattered radiation from each spot 204 onto a corresponding forward channel or detector in the optical fiber array 34' or detector array 36'. Similarly, objective 212 images the scattered radiation from each spot 204 to its corresponding backscatter fiber or detector in the fiberoptic array 34" or detector array 36". Objectives 210 and 212 may be situated so that all of the spots in the single file array of elongated illuminated spots 204 are substantially within their focal planes. As shown in FIG. 9, objective 212 can collect the forward scattered radiation and objective 210 can collect the back scattered radiation. Instead of using lenses as shown in FIG. 9, objectives 210 and 212 may also be reflective objectives.

The beamsplitter used to generate the single file array of elongated illuminated spots 204 may be oriented at −45 degrees with respect to the plane of incidence so that the spots (as differentiated from the spot orientation of FIG. 9) would form a single file array oriented at −45 degrees to direction 202, and line 204b connecting the centers of the spots at such new locations is also at substantially −45 degrees with respect to the plane of incidence.

If the beamsplitter for generating the single file array of elongated illuminated spots 204 is oriented at 45 degrees with respect to the plane of incidence, collection objectives 210 and 212 may also be rotated by 90 degrees so that the single file array of elongated illuminated spots 204 arranged with their centers along the line 204b would again be within their focal planes. In such an arrangement, these objectives would again collect radiation scattered in directions substantially perpendicular to line 204b.

Instead of collecting and imaging scattered radiation in directions perpendicular to the line joining the centers of the single file array of elongated illuminated spots 204 as described above, it is also possible to collect and image the scatter radiation in a double dark field configuration. In such a configuration, the two objectives would be at locations indicated in dotted lines 210' and 212' where scattered radiation is collected substantially at +90 and −90 degrees azimuthal angle relative to the illumination beams as they reach the surface. The fiber channels or detectors have been omitted in such configuration to simplify the figure. In a double dark field configuration, different spots along the line 204a or 204b may be located at different distances from the objectives so that at least some of them will be out of focus. Even though some of the spots in the single file array of elongated illuminated spots 204 will be out of focus or somewhat out of focus, this may not have significant adverse effects on some applications, such as unpatterned surface inspection. Only one of the two objectives 210 and 212 (or 210' and 212') may suffice for some applications, and thus one of the two objectives can be omitted.

Figure 10:
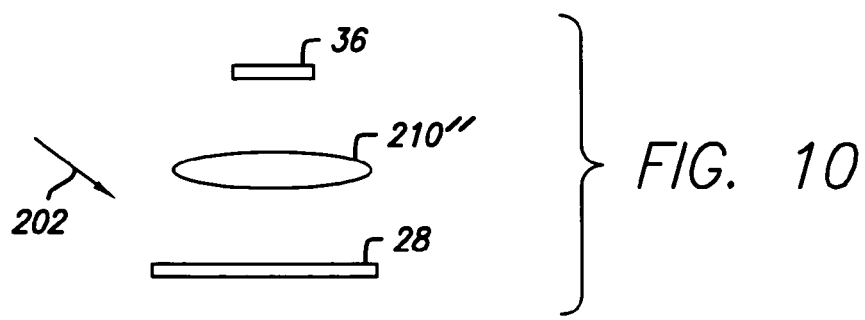
FIG. 10 is a schematic side view of an optical inspection and imaging system in a single dark field configuration.

Collection optics 210" and a detector array 36 or a collection of individual detectors (not shown) may be placed directly above the area of the surface of sample (and therefore in the plane of incidence of beams along direction 202) and inspected using a single dark field configuration to detect surface anomalies, such as in the configuration shown in FIG. 10. In such a configuration, collection optics 210" image the scattered radiation to the detector array or detector collection in at least one direction substantially normal to the surface. Preferably the collection optics 210" used has a large numerical aperture for increased sensitivity.

If the illumination beams are polarized, a polarizer may be positioned between each of the two objectives 210 and 210' and their corresponding fiber or detection channels. Thus, in the presence of a dielectric material such as silicon oxide, circularly polarized radiation in the illumination beam may be preferable. The presence of small defects may cause P-polarized radiation to be more efficiently scattered. If S-polarized radiation is employed in the illumination beams, scattering caused by the presence of roughness on the surface can be further suppressed if only S-polarized light is collected. Polarizers may be placed in the paths of beams 24 and polarizers 220 and 222 may be placed in the collection path for enabling the detection of polarized radiation components, which may in turn indicate the type of anomalies present on the wafer. Corresponding polarizers may be placed along the collection paths in the double dark field arrangements. Instead of using refractive objectives such as lenses 210, 210', 212, 212', reflective objectives may be used for collection over a large wavelength range.

A polarizer may also be placed between objective 210" and its corresponding fiber or detection channel in a fashion similar to that described above. In this case, the polarizer is constructed to pass light polarized either radially or tangentially from the surface normal. Such a polarizer can provide benefits in defect detection similar or identical to those described above for polarizers 220 and 222.

Enhanced Inspection and Imaging

The spot configuration of FIG. 9 are in focus, with all spots of approximately the same size, at the surface of specimen or wafer 28. Therefore, the focal plane of the incidence objective is at approximately 45 degrees to the optical axis, creating significant challenges in manufacturing, implementation, and alignment.

Figure 11:
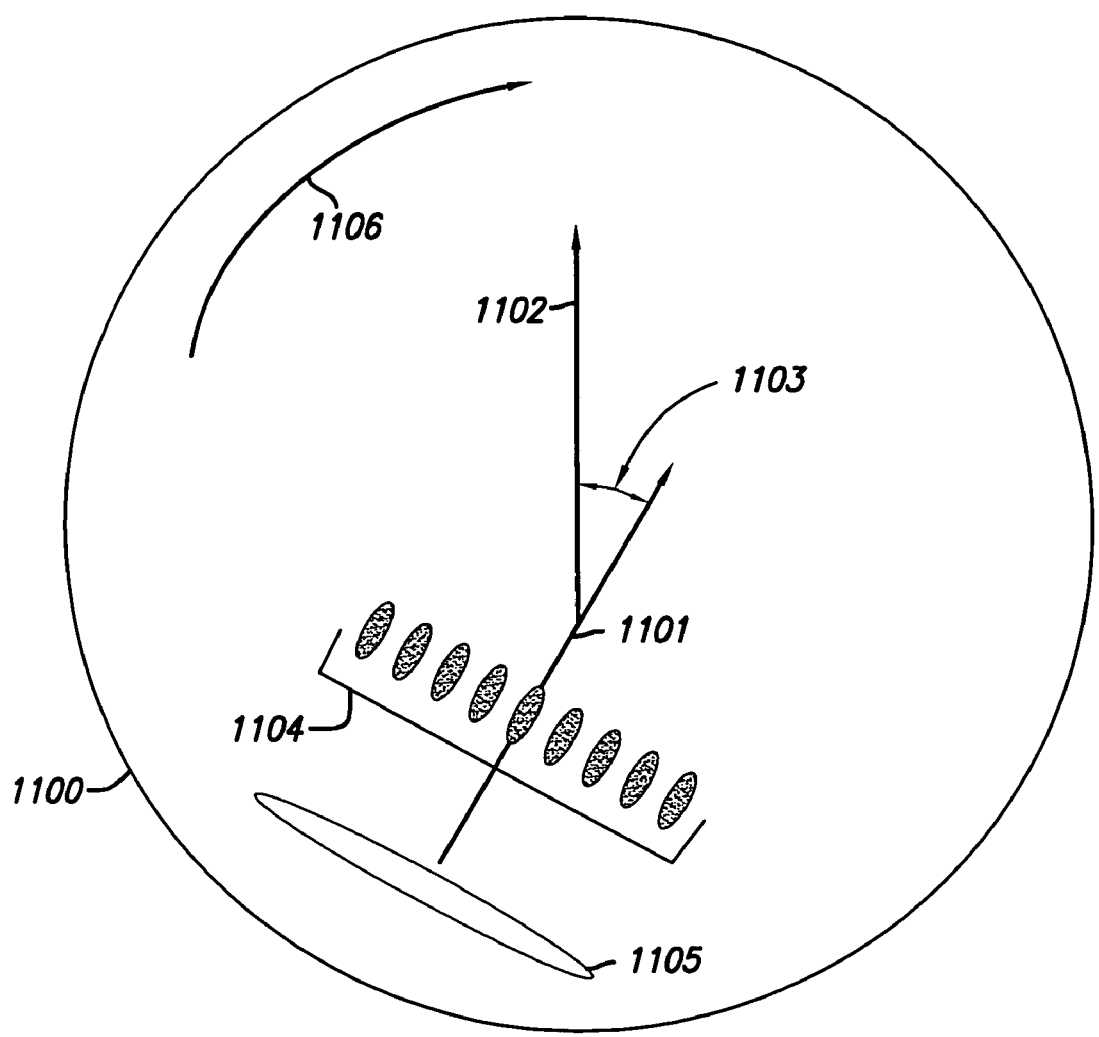
FIG. 11 illustrates a not insubstantially angularly offset orientation of stage axis, optical axis, and spot positions in accordance with the present design.

FIG. 11 illustrates a design inclining the optical axis 1101 from the objective 1105 positioned above the surface of the specimen or wafer 1100 at an angle relative to the stage axis 1102, also called a linear stage axis or linear axis. The design of FIG. 9 provides an optical axis substantially parallel to the stage axis. While the single file array of elongated illuminated spots 204 in FIG. 9 is represented by a series of lines as the spots, in actuality the spots tend to resemble ovals, or circles of Gaussian distribution as shown in FIGS. 9 and 11. The ovals do not overlap one another, but instead leave spaces or uninspected regions when the scan proceeds at an optical axis parallel to the stage axis such as is shown in FIG. 9. If, as in FIG. 11, the optical axis 1101 is not parallel to the stage axis 1102, but instead offset by an offset angle 1103 of, for example, several degrees, typically more than one degree but dependent upon the spot size employed, the spot separation employed, and the desired sample spacing in the acquired data, the trajectories of the spots in the single file array of elongated illuminated spots 1104 will address blank space between the spots without overlapping scanned regions. The focal plane of the spots in such an arrangement remains substantially perpendicular to optical axis 1101. Circular arrow 1106 indicates that the design may be employed in a spiral scan, such as by the specimen or wafer rotating with the single file array of elongated illuminated spots 1104 projected thereon.

Typical currently available telecentric objectives, or possibly the non-telecentric doublet objectives described herein, can provide performance sufficient for this offset spot orientation design. Collection of scattered radiation may be restricted to the arrangement shown in FIG. 10. However, an objective axi-symmetric with respect to wafer normal such as the objective in FIG. 10 can provide a sufficiently large solid angle of collection as compared with other collector locations suggested in FIG. 9. The objective of FIG. 10 generally provides sufficient sensitivity and can be employed as objective 1105 in FIG. 11, and may offer improved performance over the objective of FIG. 9 even if the NA is somewhat restricted by the obliquely incident beams due to working distance limitations.

Using the objective of FIG. 10 as objective 1105, a Fourier plane may be formed in the collection optics. Spatial filtering may be employed to create effects similar to a double dark field arrangement, and such an arrangement may be employed in the case of, for example, rough metal films. Furthermore polarizers may be employed in the collection optics to provide sensitivity benefits similar to those described in relation to FIGS. 9 and 10.

Such a design may be employed in circular or spiral inspections as well as traditional Manhattan geometry inspections. In the case of a spiral scan, the angular offset between the optical axis and the linear stage axis may need to be adjusted as a function of rotary stage speed, linear stage speed, spot size, and separation to keep the sample spacing of the acquired data at a predetermined size. In the case of a linear scan, the angular offset between the optical axis and the linear stage axis may need to be adjusted as a function of spot size and spot separation to keep the sample spacing of the acquired data at a predetermined size. If the field size of the objective is sufficiently large, such as when the objective resolution is less than diffraction limited, the angle between the optical axis 1101 and the stage axis 1102 may be relatively small. Such an arrangement may limit the resultant footprint and chance of overlap during inspection and data collection. Any tilt of the major and minor axes of each substantially Gaussian spot or spots relative to the spiral tracks may be resolved using post processing.

The present design may be employed in various environments, including but not limited to semiconductor wafer inspection/lithography, biological inspection, medical research, and the like.

While the invention has been described above by reference to certain embodiments, it will be understood that changes and modifications may be made without departing from the scope of the invention, which is to be defined only by the appended claims and their equivalents. For example, while the embodiments are illustrated with respect to wafer anomaly detection, the invention may be used for anomaly detection on other types of surfaces as well, such as flat panel displays, magnetic and optical heads, disks and so on. All of the references referred to above are incorporated herein by reference in their entireties. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A method for detecting anomalies of a surface, comprising:

focusing at least one illumination beam along an optical axis into a linear array of illuminated elongated spots on the surface, each illuminated elongated spot oriented substantially parallel with each other illuminated elongated spot along a line perpendicular to the optical axis, wherein the illuminated elongated spots are spaced apart from one another and elongated in a direction substantially parallel to the optical axis;

performing a scan along a linear axis, wherein the linear axis is offset from the optical axis and from the elongation direction of the illuminated elongated spots by a nonzero angular quantity, wherein performing the scan enables scanning substantially all portions of the surface in the presence of spacing between the illuminated elongated spots;

imaging scattered radiation from said spots onto an array of receivers; and providing scattered radiation information from said scattered radiation imaging to processing equipment.

2. The method of claim 1, wherein said focusing focuses the beams at an oblique angle of incidence to the surface.

3. The method of claim 1, wherein said imaging images the scattered radiation along one or more directions substantially normal to a substantially straight line of focused beams.

4. The method of claim 1, where said imaging includes forming an intermediate Fourier image plane before the array of receivers.

5. The method of claim 4, where Fourier filtering of the scattered radiation is performed proximate the Fourier image plane.

6. The method of claim 1, wherein the scattered radiation from said spots is imaged by reflective optics.

7. The method of claim 1, further comprising selecting a wavelength and supplying the illumination beams of radiation so that the radiation comprises a component of the selected wavelength in a UV, deep UV, visible or infrared wavelength range, said supplying comprising passing a beam of radiation of the selected wavelength component through a diffracting element to form the illumination beams.

8. The method of claim 7, further comprising altering the selected wavelength of the wavelength component of the illumination beams focused in the focusing, and replacing the diffracting element by another diffracting element so that spot separation of the said spots remain substantially unchanged by the altering.

9. The method of claim 1, said method further comprising causing rotational motion between the surface and the beams so that the spots scan over partially overlapping paths.

10. The method of claim 9, wherein the causing causes rotational motion of the surface while leaving the beams at substantially stationary positions.

11. The method of claim 1, wherein the focusing comprises focusing the beams to a patterned semiconductor wafer.

12. The method of claim 1, said surface comprising a surface of an unpatterned semiconductor wafer, wherein the focusing comprises focusing the beams to the surface in directions that are oblique to the surface and so that at least one dimension of the spots is not less than about 5 microns.

13. The method of claim 1, wherein said focusing focuses polarized radiation, and said imaging comprises passing the scattered radiation through a polarizer.

14. An apparatus for detecting anomalies of a surface, comprising:
    illumination optics focusing illumination beams along an optical axis to a linear array of spots on the surface, each spot oriented substantially parallel with each other along a line perpendicular to the optical axis, wherein the illumination optics elongate the linear array of spots substantially parallel to the optical axis and each spot is spaced apart from each other spot in the linear array of spots;
    imaging optics imaging scattered radiation from said spots onto an array of receivers; and
    processing equipment configured to receive and process scattered radiation information from said array of receivers;
    wherein performing a linear scan using the illumination optics occurs along a linear axis, and further wherein the linear axis is offset from the optical axis and from the elongation direction of the elongated spots by a nonzero angular quantity, and performing the scan enables scanning substantially all portions of the surface in the presence of spacing between the illuminated elongated spots.

15. The apparatus of claim 14, wherein said imaging optics comprise a curved reflective surface.

16. The apparatus of claim 14, further comprising means for supplying a beam of radiation of a selected wavelength in a UV, deep UV, visible or infrared wavelength range, and a diffracting element that diffracts the beam of radiation of the selected wavelength component to form the illumination beams.

17. The apparatus of claim 16, said supplying means comprising an optical source that supplies radiation of a wavelength selectable from a plurality of wavelengths, said apparatus comprising a plurality of diffracting elements, each element designed to diffract radiation at one of the plurality of wavelengths so that spot separation of the spots remains substantially unchanged when the source selects and supplies radiation substantially at a different one of the plurality of wavelengths than previously.

18. The apparatus of claim 14, said illumination optics comprising a first objective, said imaging optics comprising a second objective having a numerical aperture larger than that of the first objective.

19. The apparatus of claim 18, wherein said imaging optics images scattered radiation from said spots onto the array of receivers without employing the first objective.

20. The apparatus of claim 14, said apparatus further comprising an instrument causing rotational motion between the surface and the beams so that the spots scan over partially overlapping paths.

21. The apparatus of claim 20, wherein the instrument causes rotational motion of the surface while leaving the beams at substantially stationary positions.

22. The apparatus of claim 20, wherein the imaging optics is substantially rotationally symmetric about the rotational axis.

23. The apparatus of claim 14, where a Fourier image plane is formed within the imaging optics before the array of receivers.

24. The apparatus of claim 23, where Fourier filtering of the scattered radiation is performed proximate the Fourier image plane.

25. A method for detecting anomalies of a surface, comprising:
    focusing at least one illumination beam along an optical axis into a linear array of illuminated elongated spots on the surface, each illuminated elongated spot oriented substantially parallel with each other illuminated elongated spot along a line perpendicular to the optical axis, wherein the illuminated elongated spots are spaced apart from one another and elongated in a direction substantially parallel to the optical axis;
    performing a scan relative to a linear axis, wherein the linear axis is offset from the optical axis and from the elongation direction of the illuminated elongated spots by a nonzero angular quantity, wherein performing the scan enables scanning substantially all portions of the surface in the presence of spacing between the illuminated elongated spots;
    imaging scattered radiation from said spots onto an array of receivers so that each receiver in the array receives scattered radiation; and
    providing scattered radiation information from said imaging to processing equipment.

26. The method of claim 25, wherein said focusing focuses the beams at an oblique angle of incidence to the surface.

27. The method of claim 25, wherein said imaging images the scattered radiation along one or more directions substantially normal to a substantially straight line of focused beams.

28. The method of claim 27, where said imaging includes forming an intermediate Fourier image plane before the array of receivers.

29. The method of claim 28, where Fourier filtering of the scattered radiation is performed proximate the Fourier image plane.

30. The method of claim 25, wherein the scattered radiation from said spots is imaged by reflective optics.

31. The method of claim 25, further comprising selecting a wavelength and supplying the illumination beams of radiation so that the radiation comprises a component of the selected wavelength in a UV, deep UV, visible or infrared wavelength range, said supplying comprising passing a beam of radiation of the selected wavelength component through a diffracting element to form the illumination beams.

32. The method of claim 31, further comprising altering the selected wavelength of the wavelength component of the illumination beams focused in the focusing, and replacing the diffracting element by another diffracting element so that spot separation of the said spots remain substantially unchanged by the altering.

33. The method of claim 25, said method further comprising causing rotational motion between the surface and the beams so that the spots scan over partially overlapping paths.

34. The method of claim 33, wherein the causing causes rotational motion of the surface while leaving the beams at substantially stationary positions.

35. The method of claim 25, wherein the focusing comprises focusing the beams to a patterned semiconductor wafer.

36. The method of claim 25, said surface comprising a surface of an unpatterned semiconductor wafer, wherein the focusing comprises focusing the beams to the surface in directions that are oblique to the surface and so that at least one dimension of the spots is not less than about 5 microns.

* * * * *